United States Patent [19]

Brighton et al.

[11] 4,442,846
[45] Apr. 17, 1984

[54] DISTRIBUTED PORT BONE-PIERCING CATHODE FOR ELECTRICALLY STIMULATED OSTEOGENESIS

[75] Inventors: Carl T. Brighton, Malvern; Jonathan Black, King of Prussia, both of Pa.

[73] Assignee: University of Pennsylvania, Philadelphia, Pa.

[21] Appl. No.: 320,110

[22] Filed: Nov. 10, 1981

[51] Int. Cl.³ .............................................. A61N 1/04
[52] U.S. Cl. ................................. 128/784; 128/419 F
[58] Field of Search ............ 128/82.1, 419 F, 784–786

[56] References Cited

U.S. PATENT DOCUMENTS 3,842,841 10/1974 Brighton et al. ................ 128/419 F
3,918,440 11/1975 Kraus ............................ 128/419 FX

FOREIGN PATENT DOCUMENTS 60500 3/1975 Australia ........................ 128/419 F

OTHER PUBLICATIONS

Zimmer USA, Literature No. B-2360-1, 1979.
Brighton et al, "Electrically Induced Osteogenesis . . . ", 24th Annual ORS, Dallas, Texas, Feb. 21–23, 1978, p. 30.

*Primary Examiner*—Lee S. Cohen
*Attorney, Agent, or Firm*—Ferguson, Baker, Whitham & Spooner

[57] ABSTRACT

Disclosed is an improved bone-piercing cathode for providing electrical stimulation of osteogenesis at a plurality of locations. A conventional bone-piercing cathode is modified by adding a number of "ports" extending through the insulative covering to expose the cathode permitting a flow of osteogenesis stimulating current therethrough. In a preferred embodiment, seven ports are spaced three on one side and four on the other of a conventional bone-piercing cathode which is inserted into the fracture site. Sufficient current is supplied to the cathode in order to insure that each port as well as the insulation-bare wire junction can supply 20 microamperes of osteogenesis stimulating current into the body tissues. This permits bone growth stimulation adjacent a plurality of sites on the cathode.

8 Claims, 5 Drawing Figures

DISTRIBUTED PORT BONE-PIERCING CATHODE FOR ELECTRICALLY STIMULATED OSTEOGENESIS

BACKGROUND OF THE INVENTION

The present invention relates generally to the electrical stimulation of bone growth and specifically to an improved cathode which can be located precisely at the fracture site.

It has been known for some time that the provision of a direct current flowing from a cathode at or near a bone fracture to an anode taped to a patient's skin will stimulate bone growth at the fracture site with a direct current from 5 to 20 microamperes. U.S. Pat. No. 3,842,841 issued to Brighton et al., on Oct. 22, 1974, entitled "Constant Current Power Pack for Bone Healing and Method of Use" discloses such a system. A publication by Zimmer . USA, Inc., Literature No. B-2360-1, revised in September, 1979 and available from Zimmer . USA, 727 N. Detroit Street, P.O. Box 708, Warsaw, Ind. 46580, provides a detailed discussion of direct current bone growth stimulation and an advantageous system to implement such stimulation.

Briefly, the disclosed system utilizes a plurality of cathodes equipped with a drill tip which can be inserted into the fracture site. In preferred embodiments, the drill tip first goes through bone tissue and then into the fracture site. A suitable power pack is connected to each of the four cathodes and, in the preferred embodiment, a 20 microampere current is supplied to each of the four cathodes. An anode pad is placed some distance from the cathode location and serves to complete the direct current circuit. Such a system has been found to be extremely beneficial in stimulating osteogenesis, especially in the case of an extended nonunion of a fracture (two years or more).

Obviously, when four separate cathodes are inserted into or towards the fracture site, these provide four possible sources of infection and/or local irritation. Additionally, there are four cathodes which must be maintained in the proper position in order to stimulate the osteogenesis at the desired location. If only a single cathode is used, the maximum applicable current is 20 microamperes and higher amounts of current result in tissue necrosis and localized burning in the event of high current densities.

It was reported by Brighton, et al., at the Annual Meeting of the Orthopaedic Research Society, in Dallas, Tex., Feb. 21, 1978 that the actual length of the cathode did not seem to affect the amount of bone formed when non-drill cathodes were inserted in the medullary canal of test animals. It was found that, where the current level of a conventional cathode was increased, there was no increase in new bone formed and rather extensive tissue necrosis occurred at higher current values. This was not true where a single cathode had a number of small bare spots along the length of the cathode. In this configuration, a single cathode would produce the same amount of bone at each bare spot as would the conventional cathode having just a single insulation-bare wire junction. Further studies showed that the bare area at the insulation-bare wire junction on a conventional cathode was a very small area and the length of the bare wire extending beyond this insulation-bare wire junction was irrelevant to bone formation. A protein precipitate forms over the remainder of the bare wire such that current density at the end of the cathode is independent of the length of the exposed wire extending beyond the insulation-bare wire junction.

An experimental cathode was tested as reported in the above-referenced Annual Meeting, which cathode was completely covered with an insulation material with the exception of eight bare spots in the insulation which exposed the cathode. This experimental electrode was useable only in comparison with the other test electrodes in the medullary canal which easily accepted the wire cathode. It was clear that such an electrode was not readily useable in the treatment of fractures either in animals or humans without further research and development. Because the medullary canal in the test animals is not considered a fracture model, no conclusions or suggestions could be drawn regarding fracture site osteogenesis from the Annual Meeting report. The problem of initially locating the cathode in the vicinity of the fracture site and maintaining its position therein is not addressed in the report and, of course, is critical in any clinical application of such a cathode.

SUMMARY OF THE INVENTION

It is therefore an object of the present invention to provide a method for quickly and easily inserting a multiple port cathode into the fracture site in a human patient such that the cathode is maintained in place.

It is a further object of the present invention to provide a single cathode which can provide greater than 20 microamperes of direct current osteogenesis stimulation to a fracture site without causing necrosis or tissue destruction.

It is a still further object of the present invention to provide a single cathode capable of being utilized with existing cathode drill equipment which will effectively utilize greater than 20 microamperes of current and cause larger amounts of bone growth than could be expected with a 20 microampere current.

It is a further object of the present invention to provide a distributed cathode which will stimulate osteogenesis over an area greater than that stimulated by a single cathode, and is applicable to non-medullary insertion situations.

The above and other objects were achieved by providing a single cathode having a plurality of ports spaced thereupon in combination with a drill tip to enable the cathode to be placed through bony tissue if necessary. In a preferred embodiment, seven ports in the cathode insulation plus the insulation-bare wire junction provide eight exposures of the cathode to skin and bone tissue. A current of 160 microamperes when connected to the cathode, provides 20 microamperes in current flowing from each port and the insulation-bare wire junction to optimally stimulate osteogenesis through the distribution of the ports.

BRIEF DESCRIPTION OF THE DRAWINGS

A more complete appreciation of the invention, and many of the attendant advantages thereof, will be readily apparent by reference to the accompanying drawings wherein.

DETAILED DESCRIPTION OF PREFERRED EMBODIMENTS

Figure 1:
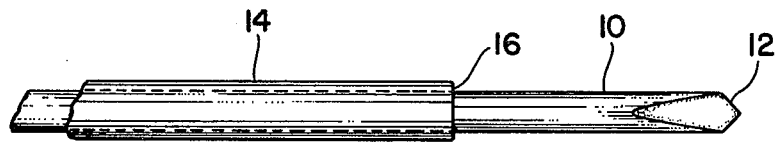
FIG. 1 is a side view of a prior art bone-piercing cathode.

Referring now more particularly to the drawings, wherein like numerals represent like elements throughout the several views, FIG. 1 is a side view of a previously known drillable cathode as discloed in the Zimmer . USA publication previously noted. A cathode 10 comprised of a conductive biocompatible material such as stainless steel is flattened and sharpened to produce a drill bit 12 at the end thereof. A biocompatible non-conductive material 14 may be Teflon® or other such insulative material. The insulation-bare wire junction 16 is the area at which the major osteogenesis stimulation takes place and the distance between this junction 16 and drill tip 12 does not appear to affect the amount of osteogenesis or the current dispersing capability of the cathode. The term "biocompatible material" for the purposes of this specification and claims means a material which shows acceptable acute and chronic local tissue response.

Figure 2:
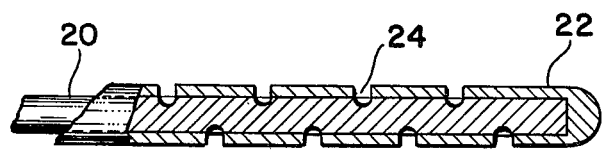
FIG. 2 is a side view of a prior art distributed port non-bone-piercing cathode.

FIG. 2 illustrates the multi-port cathode referred to in the Annual Meeting of the Orthopaedic Research Society previously mentioned. Here a stainless steel cathode 20 is covered with insulation 22 with the exception that a number of small apertures or ports 24 have been made in the insulation such that a small portion of the cathode 20 is exposed thereby. As has previously been noted, this cathode is useful for insertion in the medullary canal in test animals but has not proven useful in a clinical application because of the difficulty in locating this distributed cathode in the vicinity of a fracture site.

Figure 3:
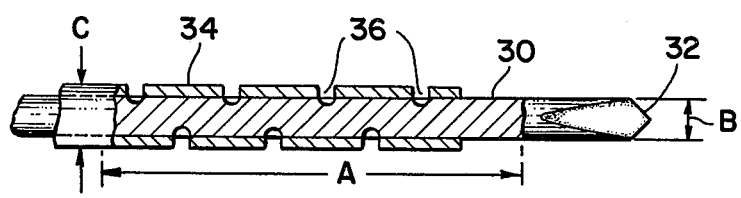
FIG. 3 is a side view of the bone-piercing distributed port cathode in accordance with the present invention.

FIG. 3 illustrates the present invention which comprises cathode 30 which may be of any suitable biocompatible conductive material such as stainless steel, titanium, etc., having a drill tip 32 at the end thereof. A suitable biocompatible insulation 34 such as Teflon®, silicone, ceramics, etc., encases the shaft of cathode 30 as shown. A series of ports 36 or apertures in the insulation are provided such that a small portion of cathode shaft 30 is exposed to the surrounding tissue. The utilization of drill point 32 with the distributed port arrangement shown in FIG. 3 permits the distributed cathode to be placed directly across or through a fracture site which serves to promote osteogenesis throughout the range A as shown in FIG. 3. The width of the drill point 32 (dimension B) is equal to or slightly larger than the width of the insulation (dimension C) and is preferably equal thereto in order that the cathode be securely retained after insertion.

Figure 4:
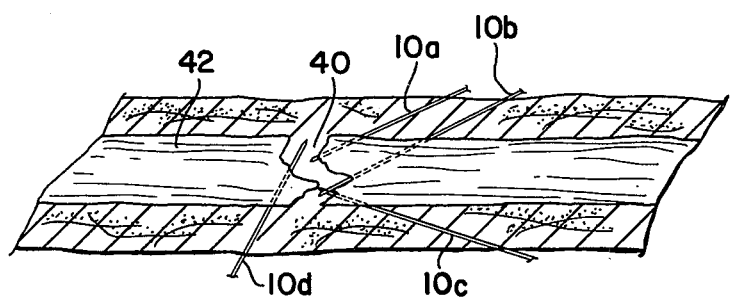
FIG. 4 is a side illustrational view of the prior art method of electrical stimulation of bone growth across a fracture site.

FIG. 4 illustrates a fracture in which the prior art cathodes in FIG. 1 are located in the fracture site 40 of bone 42. It will be noted that four of the prior art electrodes are needed to provide osteogenesis stimulation across the entire site of the fracture, since each cathode provides osteogenesis at its tip only. The utilization of a single extended cathode tip electrode across the fracture site would still result in osteogenesis stimulation at the insulation-bare wire junction only. The utilization of the multi-port distributed cathode illustrated in FIG. 2 would require a surgical invasive procedure placing the cathode at the proper position with some external means for maintaining the cathode in the desired position.

Figure 5:
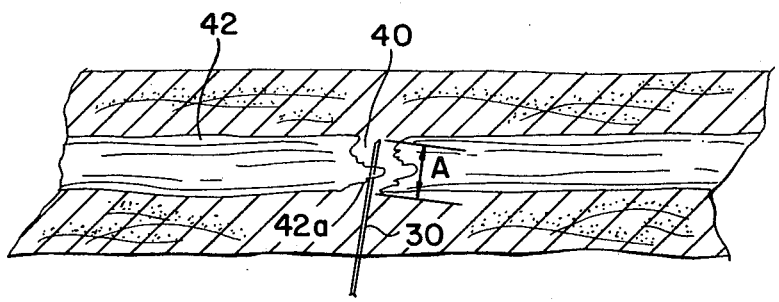
FIG. 5 is a side illustrational view of the present method of electrical bone growth stimulation across a fracture site using the present invention.

FIG. 5 illustrates the use of the present invention. A single cathode 30 with multiple ports 36 thereon is drilled through bony tissue at 42a securely positioning the cathode in the site of the fracture 40. The ports are distributed over a portion of the length of the cathode such that there is an effective region stimulating osteogenesis across the entire fracture site as indicated by Region A in FIG. 5. Thus, only a single cathode insertion is necessary in order to treat this fracture with the cathode of FIG. 3 as opposed to four or more cathodes which would be necessary in the prior art. It should be noted that, in a preferred embodiment, the cathode 30 in FIG. 5 would have n ports located thereon with a current of $(n+1) \times 20$ microamperes supplied thereto in order to obtain 20 microamperes of current at each port and at the insulation-bare wire junction. It is understood that each of the separate cathodes in FIG. 4 would have 20 microamperes applied to each one in order to stimulate osteogenesis at each cathode's insulation-bare wire junction.

An additional difficulty with placement of prior art cathodes as shown in FIG. 4 is that care must be taken that the uninsulated tips of the cathodes do not touch each other, and, an optimum placement is a minimum separation distance between each cathode's insulation-bare wire junction of 0.5 cm. With the present invention shown in FIG. 3, the optimum distance between the insulation-bare wire junction and the ports is already set by virtue of the manufacture of the cathode 30 and thus it is unnecessary to exert the care required of the prior art cathodes in determining cathode insulation-bare wire junction positioning.

In view of the above discussion, it can be seen that the present invention provides an implantable cathode which, by virtue of being drilled through bony tissue, is fixably positioned in the desired fracture location. By virtue of its including a plurality of ports, the single cathode can disburse 20 microamperes of current at each port and at its insulation-bare wire junction and thus accommodate a much larger total current input to the single cathode than prior art cathodes. Additionally, the single cathode can provide much higher osteogenesis stimulation than can seven conventional cathodes 10 inserted into the fracture site (assuming the present invention is configured as shown in FIG. 3 with seven ports and the insulation-bare wire junction). Obviously, a greater or smaller number of ports could be utilized and the amount of current applied to the cathode raised or lowered in accordance therewith. The distribution of ports along a cathode could vary depending upon the length of the fracture and the area over which osteogenesis is desired. In a preferred embodiment as illustrated in FIG. 3, the spacing between ports on the same side of the cathode is 1.0 cm with the closest port being located 0.5 cm from the insulation-bare wire junction. In the embodiment illustrated in FIG. 3, the ports are hemispherical and formed by cutting away the Teflon® with a 0.20 mm radius ball end cutter to form a hemispherical dimple 0.41 mm in diameter in the wire surface. Cylindrical non-dimpled ports have also proven effective. In the embodiment illustrated in FIG. 3, where n=7, in accordance with the previously discussed formula, a constant current source of 160 microamperes would be connected to the portion of the cathode extending from the surface of the patient's skin.

In view of the above technology, many modifications of the drill bit equipped distributed port cathode will be obvious to one of ordinary skill in the art. Therefore, the present invention is not limited to the embodiments and applications expressed herein and is only limited in accordance with the appended claims.

The embodiments of the invention in which an exclusive property or privilege is claimed are defined as follows:

1. A cathode for use in stimulating osteogenesis in the vicinity of a human fracture site when connected to a suitable current source, said cathode comprising:
   a biocompatible conductor means for drilling through bony tissue layers having at least one end; and
   biocompatible non-conducting means for insulating said conductor means, said insulating means generally covering said conductor means except in the vicinity of said at least one end, said insulating means further including means for defining at least one port in said insulating means exposing a portion of the surface of said conductor means.

2. A cathode in accordance with claim 1, wherein said conductor drilling means comprises:
   tip means, at said at least one end, for drilling through bone, said tip means having a width; and
   shaft means for transmitting drilling torque to said tip means.

3. A cathode in accordance with claim 2, wherein said insulating means generally covers said shaft means and has a width not greater than the width of said tip means.

4. A cathode in accordance with one of claims 1 through 3, wherein said port defining means defines a plurality of ports in said insulating means.

5. A cathode in accordance with claim 4 wherein said insulating means comprises Teflon ® and said ports are hemispherical in shape, 0.41 mm in diameter and 0.20 mm in depth.

6. A cathode in accordance with claim 2 or claim 3, wherein said tip means comprises a flattened and sharpened end portion of said shaft means.

7. A cathode in accordance with claim 6, wherein said port defining means defines a plurality of ports in said insulating means and said insulating means comprises Teflon ®.

8. A cathode in accordance with claim 7, wherein said width of said tip means is equal to a width of said shaft means including said insulating means and each of said ports is hemispherical in shape, 0.41 mm in diameter and 0.20 mm in depth.

* * * * *